United States Patent [19]
Kantrowitz et al.

[11] Patent Number: 5,529,533
[45] Date of Patent: Jun. 25, 1996

[54] REMOVABLE DENTAL WORK TABLE WITH VACUUM

[76] Inventors: Lawrence L. Kantrowitz, 1480 Pleasant Valley Way; Edward J. Littman, 9 Syme Ave., both of West Orange, N.J. 07052

[21] Appl. No.: 375,517

[22] Filed: Jan. 18, 1995

Related U.S. Application Data

[63] Continuation of Ser. No. 795,822, Nov. 21, 1991, abandoned.

[51] Int. Cl.⁶ .................................................. B24B 55/06
[52] U.S. Cl. .................................. 451/456; 433/79
[58] Field of Search .................................. 451/456, 411, 451/413, 414, 89, 90, 88, 87, 406, 914, 361, 453

[56] References Cited

U.S. PATENT DOCUMENTS

| | | |
|---|---|---|
| 951,506 | 3/1910 | Meyer. |
| 1,388,347 | 8/1921 | Klicka. |
| 1,742,331 | 6/1928 | Voigt. |
| 1,896,772 | 2/1933 | Drespel. |
| 2,059,039 | 10/1936 | Sandman. |
| 2,637,852 | 5/1953 | Globe. |
| 2,751,729 | 9/1954 | Christiansen. |
| 3,510,945 | 5/1970 | Weiss et al. ................... 433/79 |
| 4,013,328 | 3/1977 | Wolf et al. ................... 312/209 |
| 4,184,151 | 1/1980 | Kuboki. |
| 4,184,251 | 1/1980 | Kuboki ................... 51/220 X |
| 4,226,054 | 10/1980 | Coty. |
| 4,443,194 | 4/1984 | Fuchs ................... 433/79 |
| 4,653,737 | 3/1987 | Haskins et al.. |
| 4,801,265 | 1/1989 | Kratochwilla ................... 433/98 |
| 4,824,083 | 4/1989 | Catanni. |
| 4,934,933 | 6/1990 | Fuchs ................... 433/79 |
| 4,952,146 | 8/1990 | Doty ................... 433/77 |
| 5,013,240 | 5/1991 | Bailey et al. ................... 433/77 |
| 5,033,238 | 7/1991 | Zubler ................... 51/273 X |
| 5,379,815 | 1/1995 | Brazell et al. ................... 144/287 |

*Primary Examiner*—Bruce M. Kisliuk
*Assistant Examiner*—Derris H. Banks
*Attorney, Agent, or Firm*—Mathews, Woodbridge & Collins

[57] ABSTRACT

The present invention is a device which can be portable and easily attachable and removable from existing dental work station tables. The apparatus comprises a work platform which can be removably connected to the work station table. A suction tube at the work station can communicate with the surface of the work platform. The suction tube can easily be connected and disconnected from the work platform for use in treating the patient, such as providing mouth suction. The apparatus preferably is supported by a mounting means on the work table with the work platform preferably horizontal. Preferably the platform is supported by a support means through which it is attached by the mounting means to the table. The work platform thereby provides both support for the article being worked on and suction to remove debris.

14 Claims, 3 Drawing Sheets

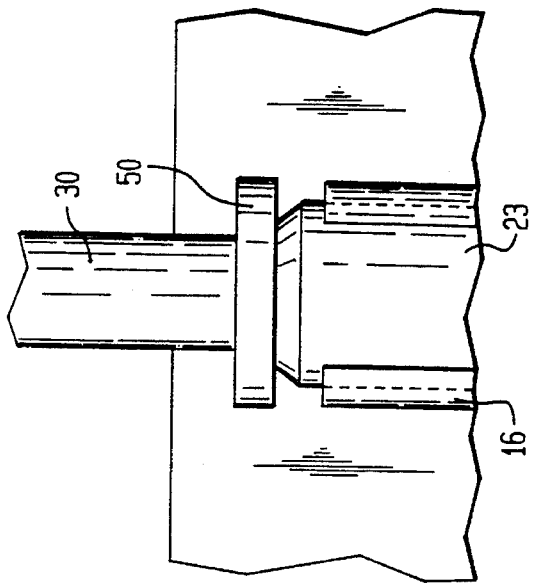
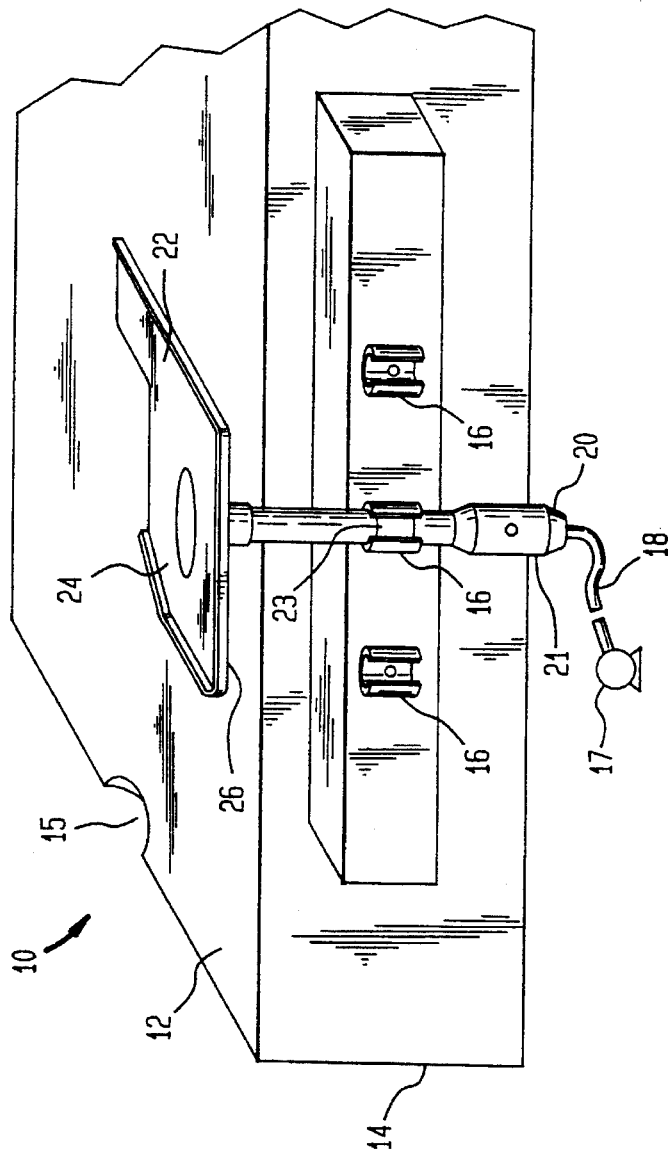

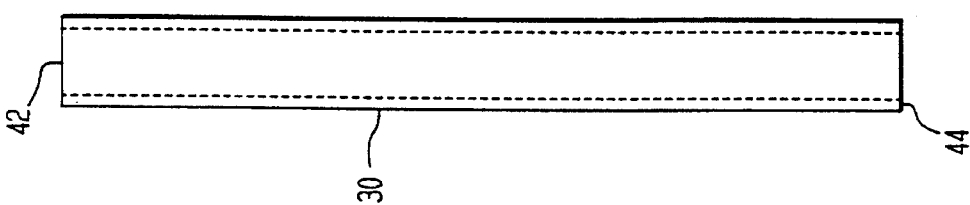
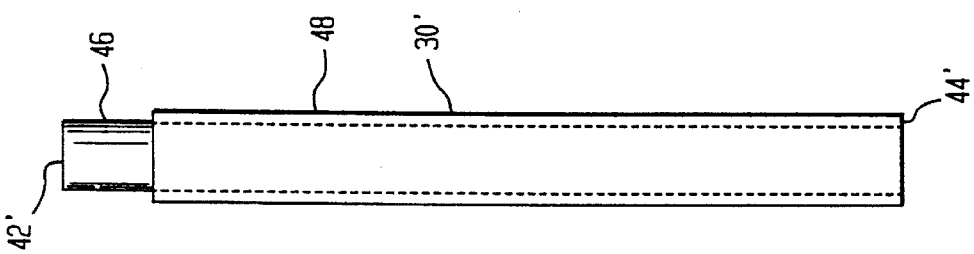
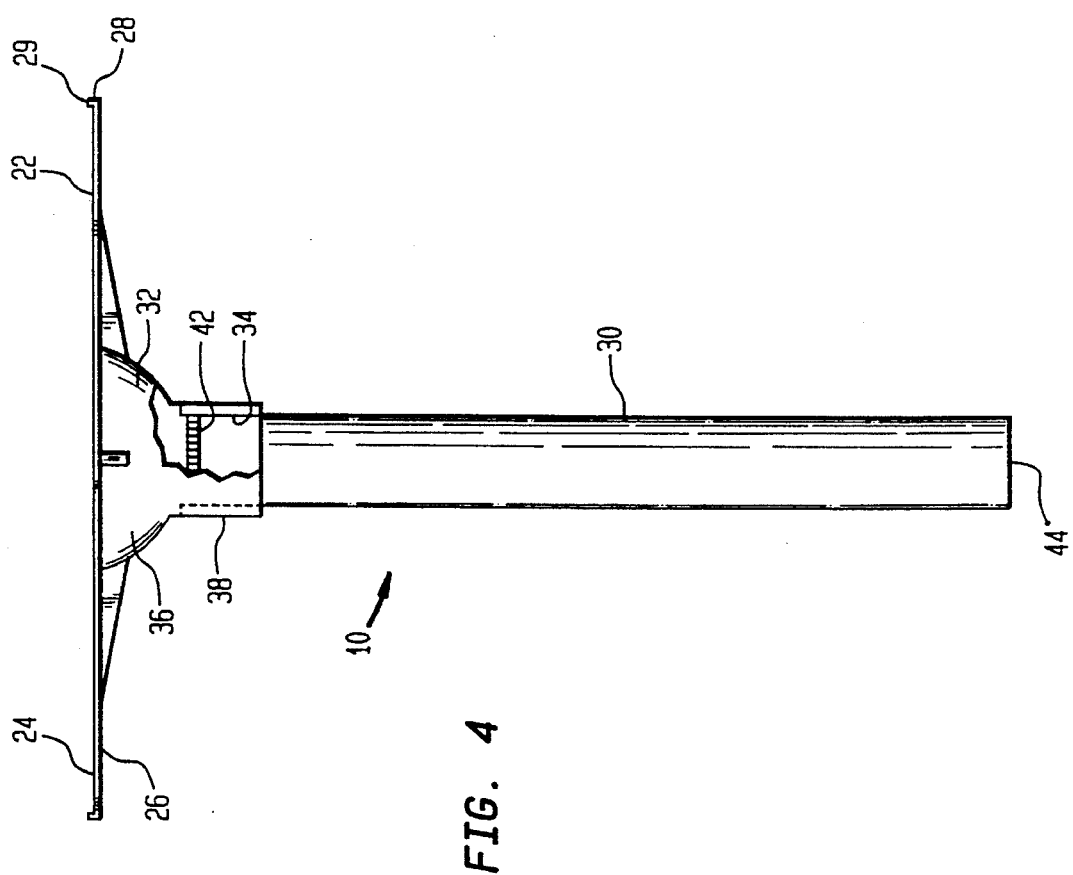

REMOVABLE DENTAL WORK TABLE WITH VACUUM

BACKGROUND OF THE INVENTION

This application is a continuation of Ser. No. 07/795,822 abandoned Nov. 21, 1991.

FIELD OF THE INVENTION

The present invention relates to a dental work table; and more particularly, a removable dental table which can be used with a vacuum.

DESCRIPTION OF RELATED ART

Dental work typically involves the treatment of a succession of patients at a dental work station. Most dental work stations contain sufficient facilities within reach of the patient and the dentist. Typically, a dental work station contains a reclining seat on which the patient is located. A substantial amount of the dental care can be conducted immediately at the work station. Such facilities include a small sink with running water and a dental work station table.

Dental work station tables are used to support a variety of the tools useful to treat the patient. Such tools include a variety of the pneumatic and electrical tools used by the dentist in treating the patient. The tools can be removably attached to the table by suitable means, such as holders, collars or clips. The most common way to attach tools is to have holders or collars at the edge of the dental work station table. This enables the dentist to pick up and replace the tools quickly and to move from one step to another without the necessity of having a nurse present or to use two hands to secure the tool in place.

Common procedures often include the cutting and grinding of materials with which the patient is treated. Such materials, for example, include prosthetic devices, caps, plates, and a variety of moldings. Cutting and grinding means are conveniently located at the dental work station table. Unfortunately, this results in waste in the form of chips, and dust. Occasionally, these chips and dust are made of valuable materials which are desirable to collect. More often the fine dust is merely waste which creates a dirty environment which must be cleaned prior to treating the next patient. Additionally, the dust can, and often does, get on the dentist and the patient and may be breathed in by all in the area.

A problem with cutting and grinding of materials at the dental work table is that it is often full of tools and material used in treating the patient. The work table is generally not designed to support the work while it is being cut or ground.

The generation of undesirable, and even desirable, waste dust in the dental industry has been recognized, for example, in U.S. Pat. No. 1,388,347 which discloses a dentist's cabinet which provides storage for tools and other requisites for all work. There is a suction means for collecting dust generated.

Another approach is shown in U.S. Pat. No. 1,742,331 where a collecting cup was used primarily to collect valuable debris when working with precious metals, such as gold crowns.

U.S. Pat. No. 1,896,772 discloses a dental slab having funnel-like cavities on the sides or corners to facilitate catching waste materials.

U.S. Pat. No. 4,184,251 discloses an instrument for processing artificial teeth and the like. The instrument collects the metallic powders or shavings produced during the processing of artificial teeth. There is no disclosure or suggestion that a suction means be used to collect the ground particles. Nor is it disclosed that this instrument be used in the proximity of the patient.

U.S. Pat. No. 4,226,054 recognizes the problem of exposure to certain grindings in the dental industry. The device comprises a portable vacuum source and interchangeable intake nozzle for attachment to hand grinder or positioning near a bench or grinder. This apparatus has no support means such as work table associated with it.

U.S. Pat. No. 4,824,083 is directed to a work rest for use by dental technicians and goldsmiths. It contains a work area, platform, and a vacuum intake associated with the platform. It is designed for use by dental technicians as a permanent fixture to a vacuum pipe at a work bench.

None of the above devices provide for temporary, easily attachable, removable work station platform for use at a dental work station in a patient operating area, in a laboratory, or jewelry work area.

SUMMARY OF THE INVENTION

The present invention is a device which can be portable and easily attachable and removable from existing dental work station tables. The apparatus comprises a work platform which can be removably connected to the work station table. A suction tube at the work station can communicate with the surface of the work platform. The suction tube can easily be connected and disconnected from the work platform for use in treating the patient, such as providing mouth suction. The apparatus preferably is supported by a mounting means on the work table with the work platform preferably horizontal. Preferably the platform is supported by a support means through which it is attached by the mounting means to the table. The work platform thereby provides both support for the article being worked on and suction to remove debris.

More specifically, the present invention includes a system or apparatus comprising a dental work station table in the patient operating area at which is located a vacuum hose having a vacuum hose end. The platform comprises a work surface which communicates with the vacuum hose end. The work platform can be removably connected to the work station table and to the vacuum hose.

The apparatus preferably comprises a support means through which the work platform is connected to the work station table. In specific embodiments the support means comprises a hollow support tube through which the vacuum hose communicates to the work surface. Preferably, the hollow support tube is connected to a connecting surface opposite the work surface of the work platform. The support means preferably raises the work platform and provides a working space beneath the work surface.

The work platform can be removably connected to the work station table by a suitable mounting means. The work station tables typically have a table top and table edges. Preferred mounting means are grooves, collars, or spring clips mounted on the side of the work station table. The suction tube fits into the groove, clip, collar or other mounting means on which it is supported. The suction tube can fit and be attached directly to the end of the support tube opposite the end connected to the connecting surface of the platform. Any suitable fitting can be used. Where the tube has an air regulator and/or aspirator at the tube end, the tube can fit directly onto the air regulator. There can be a suitable collar to prevent the tube from sliding through the mounting means, and be supported thereon. In this way the work surface of the platform can be supported by the tube on the mounting means at the edge of the work station table.

In preferred embodiments there is a depression in the work surface, such a a bowl, with the hollow support tube connected to the connecting surface of the work platform at the depression. There can be a trap or screen between the hollow support tube and the work platform. The screen can catch large objects or pieces inadvertently dropped into the bowl or depression.

In the most preferred embodiments the hollow support tube has an outer diameter which can fit into the vacuum hose end. Typical outer diameters are 0.25 to 0.50 inches. A particularly preferred outer diameter is 0.440 inches. This diameter is desirable since the suction hose can snugly fit over the tube which at the same time can fit into the groove or holder and be supported on the work table. There can be a rigid collar around the support tube which fits into common sized holders attached to the edges of the work tables.

The present invention includes a method of moveably connecting the above recited work platform to a dental work station. The work surface is connected in communication with the vacuum hose end. The work product is supported on a work platform. The work product is acted upon, i.e., ground, and waste is sucked into the vacuum hose.

The apparatus of the present invention is designed to fit easily, and removably into the grooves or other mounting means at the dental work station table. The platform is supported on the dental work station, preferably by a support which itself can be used as a means to communicate between vacuum at the dental work station to the surface of the work platform. The platform thereby provides a removable support to which vacuum means can easily be attached and detached as needed. The device enables grindings to be cleaned as they are produced for the comfort and cleanliness of the dentist, patient and the work area. The article being worked on can be supported rather than being hand held or supported on an uneven surface. The platform can be made of any suitable material including plastics which can be vacuum or injection molded. The platform can be of any suitable shape depending on the needs of as particular dentist. The whole device or its parts may be disposable, or be made of a material which can be sterilized chemically or in an autoclave.

BRIEF DESCRIPTION OF THE DRAWINGS

FIG. 1 is a view in perspective of a dental work station in combination with the work platform of the present invention.

FIG. 1A is an enlarged view showing the preferred mounting means in FIG. 1.

FIG. 4 is a side view of the work platform connected to a support means.

FIG. 5 is a side view of a preferred support means.

FIG. 6 is a side view of an alternative support means.

DESCRIPTION OF THE PREFERRED EMBODIMENTS

Figure 2:
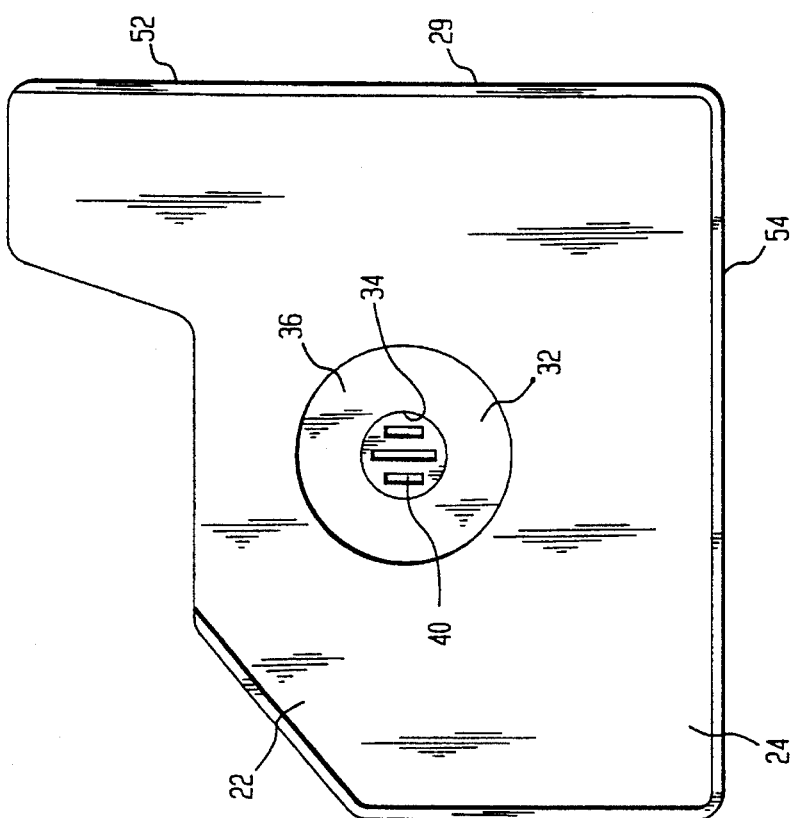
FIG. 2 is a bottom view of the portable work platform.

The present invention will be understood by those skilled in the art by reference to the embodiment illustrated in FIGS. 1 through 6.

FIGS. 1 and 1A show the apparatus 10 of the present invention used as a system at a dental work station. The apparatus comprises the dental work station table 12 having an edge 14. The edge 14 can contain mounting means such as support grooves 15, collars 16, spring clips of the like for holding a variety of dental tools such as air drills and grinders and suction related apparatus. The dental work station table 12 is located in the patient operating area so that it and the patient are easily accessible to the dentist.

There is a vacuum source 17 from which a vacuum hose 18 brings a vacuum. The vacuum hose 18 can be any suitable size and is typically made of a polymeric material. The vacuum hose has a vacuum hose end 20. The vacuum hose snugly fits around a variety of vacuum related tools, such as mouth suction devices, i.e., aspirator 21 having aspirator tip 23. Disposable fixtures can be fitted to the vacuum hose for use in the mouth of a patient. After use the disposable fixtures can be disposed and the vacuum hose readied for the next patient. Vacuum hoses come in standard sizes to enable them to be sealingly connected to a variety of standard fittings. The vacuum hose typically has an outer diameter of 0.25 to 0.625 inches and an inner diameter of 0.25 to 0.50 inches.

The apparatus 10 comprises a work platform 22. Work platform 22 comprises a work surface 24, a connecting surface 26 opposite the work surface and a peripheral edge 28. The peripheral edge 28 can have a lip or fence 29 rising from the work surface 24 around at least part of the peripheral edge 28. In the embodiments shown in FIG. 3, the lip is around only part of the surface with part of the surface ending without a lip to permit working off of a flat surface as necessary. The lip can be from ⅓₂ to ¼ and preferably ¹⁄₁₆ to ⅛ inch wide. The lip is from ⅓₂ to ¼ and preferably ¹⁄₁₆ to ⅛ inch high from the work surface. The work platform can removably or permanently connected or attached to the work station table by a suitable support means. The vacuum hose end 20 preferably communicates to work surface 24 through a support means. A preferred support means is a stiff, hollow support tube 30. The vacuum in the vacuum hose 18 communicates to work surface 24 through hollow support tube 30. The use of a support tube 30 raises the working surface and results in a working space beneath the platform. This provides room for the hands and allows better grasping and support of the work product.

Preferably, the work surface 24 comprises a depression, such as a bowl 32. The bowl can be any suitable dimension with a bowl having a radius of from 0.5 to 1.0 and preferably about ⅝ inch. There is a means to connect hose end 20 to a hole 34 passing through and having an edge defined in the depression 32. Preferably, the hose 18 communicates with the hole 34 through support tube 30. In this way, a vacuum is communicated through support tube 30, through hole 34 in depression 32, to work surface 24.

The depression 32 is preferably a concave shape bowl having a bowl portion 36 with hole 34 passing through the work surface 24 in bowl 36. The bowl 36 can have a connecting extension 38 extending around hole 34 and from the back surface 26. Preferably, the extension 38 is cylindrical in shape having an inner diameter and an outer diameter. There is preferably a screen or trap 40 located at hole 34 between hole 36 and extension 38. The trap is designed to permit dust and grindings and small cuttings to pass through to the vacuum hose while preventing the passage of larger pieces, including work product inadvertently dropped, into the bowl 36.

The preferred support means is a hollow support tube 30 which has a platform connection end 42 and a vacuum connection end 44. The tube 30 is preferably a cylindrical stiff tube. It is preferably made out of a plastic material. The tube 30 should be strong enough to support the pressure and weight placed upon the work surface 24 during normal dental grinding and cutting operations. FIG. 5, is a preferred support means having a straight tube which would fit to corresponding platform extension 38 at hole 34 as shown in FIG. 4. This does not require a taper or step down.

The platform connection end 42 can be cylindrical having an outer diameter which can be tapered so that it is narrower at end 42 and progressively wider moving along the tube toward vacuum connection end 44. There can be a corresponding taper in the inner diameter of extension 38. This enables a quick, detachable, sealed snug fit between platform connection end 32 and extension 38. In FIG. 6, platform connection end has a stepped down section 46 which steps out to support tube wider outer diameter 48.

The vacuum tube connection end 44 has an outer diameter over which the inner diameter of vacuum hose end 20 can sealingly fit. The support tube 20 can be sealingly inserted into extension 38 at platform connection end 42 and connected to vacuum tube 18 on the vacuum connection end 44.

Alternatively, as illustrated in FIGS. 1 and 1A, the vacuum connection end 44 of support tube 30 can be sealingly inserted into any suitable fitting connected to vacuum hose 18. In the embodiment illustrated in FIGS. 1 and 1A, the outer diameter of the support tube 30 snugly, and substantially sealingly fits to the aspirator tip 23 of an aspirator 21 attached to the vacuum hose end 20.

The assembled apparatus can be mounted by suitable means on dental work station table 12. Preferably, the outer diameter of tube 30 can be fit into at least one of the groove(s) 15, collar 16, or clips. The tube 30 is preferably supported by suitable mounting collars 16, located at the edge 14 of the dental work station table 12. Optionally, there can be a collar such as a plastic tube collar 50 snugly fit and around the support tube outer diameter. The plastic tube with collar 50 can be slipped into groove holder 15 up to collar 50 to secure a support fit.

A preferred support tube 30 is illustrated in FIG. 6. This tube is preferred since it has the same inner and outer dimensions along the entire length of the tube. The tube is 2 to 6 inches long with no tapered or step down section making manufacturing more economical. This tube is shown used in FIG. 4 where the tube fits in to extension 38 and abuts a lip at the bottom of bowl 36. An alternative and useful embodiment is the support tube illustrated in FIG. 5 having an outer diameter of 0.440 inches. It has a support tube outer diameter section extending from about 2 to 8, preferably 2 to 6 and most preferably for 4 inches from vacuum connection end 44.

Figure 3:
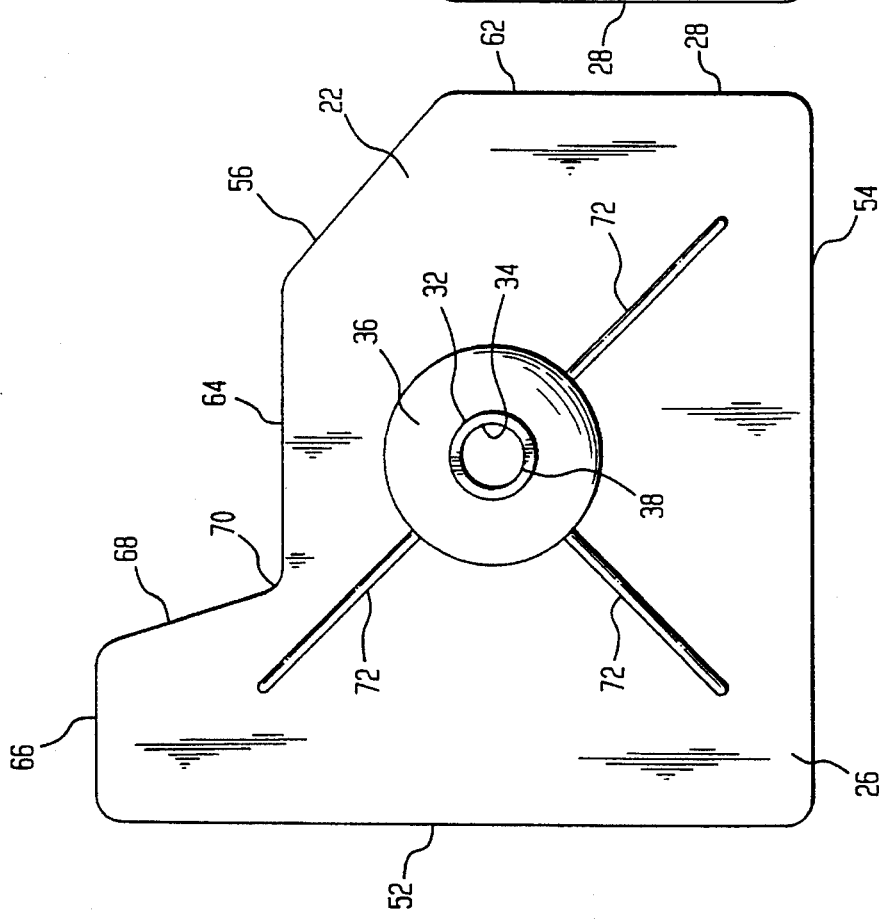
FIG. 3 is a top view of the work platform.

A preferred work platform 22 is shown in FIGS. 2 and 3 having a preferred peripheral edge 28 shape. The general shape is rectangular, preferably a square with cutout sections. This shape provides straight edges 52 and 54. There is an angular edge 56 connecting short side 62 to flat 64 which can be parallel to side 54. Flat 64 is connected to side 66 by angular edge 68. Angular edges 56 and 68 are useful to support articles being worked on, particularly angle 70 which is preferably between 90° and 180°. This design has been found to be useful in providing support, removal of dust and debris, and providing convenient edges and surfaces during cutting and grinding of dental products in the proximity of the patient. For further support the work platform 22 can have ribs or splines 72 to provide added strength. A preferred square on which the platform is based is about 3 to 6 and more preferably about 4 inches on each side.

The present invention includes a method of using the above-recited apparatus. The apparatus 10 is removably connected to a dental work station in the patient operating area. There is a vacuum hose end 18 located at the platform which is connected to the apparatus. The dental product to be worked on can be supported on the work platform 22 and cut, ground or drilled. Any waste produced can be sucked away into the vacuum hose.

In operation, the removable or detachable table top work platform can be attached to a mouth suction hose end 20 provided at the patient station or, alternatively, in the laboratory. The table allows the dentist or goldsmith, or jeweler to work on a portable, stable platform with drills or implements or anything that might create free flying particles of material, chips or dust to be suctioned immediately away from the environment. The table top can be rotated 360° for convenience to any four sides.

The apparatus overcomes the problem of the dentist or technician having to hold work on an uneven or unstable surface. More importantly, the device has incorporated a regulated source of suction cleaning the area of debris. Further, by providing a readily attachable and removable table top work station at the patients' side, the dentist can work with drills on crowns, bridges or the like in any material or compound that creates floating dust, waste and debris. The device, when it has served its purpose, can easily be removed from the hose which can changed back to its main use, i.e., a mouth suction hose.

The apparatus of the present invention can be made of any suitable material including plastic which can be vacuum or injection molded. The table top may be made in any suitable size or configuration. The whole device or parts of it may be made of a material which is disposable, sterilized with chemicals or autoclavable at temperatures up to 150° and typically up to 100°.

While exemplary embodiments of the invention have been described, the true scope of the invention is to be determined from the following claims.

What is claimed is:

1. An apparatus comprising:

a dental work station table;

a vacuum hose having a hose end;

a work platform removably connected to the work station table and the vacuum hose, the work platform comprising a work surface for supporting an object to be worked on communicating with the hose end; and a hollow rigid support tube to support the work platform and an object to be worked on through which said vacuum hose communicates with said work surface.

2. The apparatus as recited in claim 1 wherein the dental work station table comprises a mounting means to connect the work platform to the table.

3. The apparatus as recited in claim 2 wherein the work station table has an edge in which there is at least one of said mounting means into which the hollow rigid support tube fits and is supported.

4. The apparatus as recited in claim 3 wherein said hollow rigid support tube fits into the mounting means thereby supporting the work platform on the work station table.

5. The apparatus as recited in claim 4 further comprising a depression in the work surface with the hollow rigid support tube connected to the connecting surface at the depression.

6. The apparatus as recited in claim 5 further comprising a trap between the hollow rigid support tube and the work platform.

7. The apparatus as recited in claim 6 wherein the hollow rigid support tube has an outer diameter of from 0.25 to 0.50 inches.

8. The apparatus as recited in claim 7 wherein the hollow rigid support tube has an outer diameter of about 0.440 inches.

9. The apparatus as recited in claim 1 wherein said dental work station table, said vacuum hose and said work platform are made of material which can withstand temperatures of up to 150° C.

10. The apparatus as recited in claim 1 wherein said work platform is made from a material which is disposable.

11. An apparatus comprising:
   a work platform which can be removably connected to a first dental work station table and a vacuum hose at the first work station table, the work platform comprising a second work table having a work surface for supporting an object to be worked on;
   a hollow rigid support tube to support the work platform on the first work station table said vacuum hose includes a hose end the vacuum hose end communicates to the work surface through the hollow rigid support tube; and
   a means to connect the vacuum hose in communication with the work surface.

12. The apparatus as recited in claim 11 wherein the first dental work station table comprises a mounting means to connect the work platform to the first work station table.

13. The apparatus as recited in claim 11 wherein the work platform further comprises a connecting surface opposite the work surface.

14. The apparatus as recited in claim 11 further comprising a depression in the work surface with the hollow rigid support tube connected to the work surface at the depression.

* * * * *